United States Patent

Miyano et al.

Patent Number: 5,756,760
Date of Patent: May 26, 1998

[54] 1-SUBSTITUTED-2-DIPHENYLPHOSPHINONAPHTHALENE AND TRANSITION METAL COMPLEX COMPRISING THE SAME AS A LIGAND

[75] Inventors: Sotaro Miyano; Tetsutaro Hattori, both of Miyagi; Yasuko Komuro, Ibaragi; Hidenori Kumobayashi, Kanagawa, all of Japan

[73] Assignee: Takasago International Corporation, Tokyo, Japan

[21] Appl. No.: 812,549

[22] Filed: Mar. 7, 1997

[30] Foreign Application Priority Data

Mar. 7, 1996 [JP] Japan .................. 8-050312

[51] Int. Cl.$^6$ .............. C07F 9/02; C07F 15/00; C07D 207/00
[52] U.S. Cl. ............. 548/413; 548/402; 548/577; 548/578; 556/21; 556/136; 556/138
[58] Field of Search ............. 556/21, 136, 138; 548/402, 577, 578, 413

[56] References Cited

U.S. PATENT DOCUMENTS 5,510,503  4/1996  Laue et al. .................. 556/21
5,523,437  6/1996  Hayashi et al. ............. 556/21

Primary Examiner—Porfirio Nazario-Gonzalez
Attorney, Agent, or Firm—Sughrue, Mion, Zinn, Macpeak & Seas, PLLC

[57] ABSTRACT

A 1-substituted-2-diphenylphosphinonaphthalene represented by formula (I):

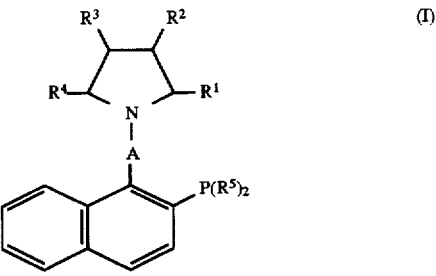

wherein at least one of $R^1$, $R^2$, $R^3$, and $R^4$, which may be the same or different, represents a lower alkyl group having 1 to 4 carbon atoms which may be substituted with an alkoxy group, a phenyl group or —$OR^6$ (wherein $R^6$ represents a hydrogen atom, a lower alkyl group having 1 to 4 carbon atoms or an alcohol-protective group), and the rest of them represent a hydrogen atom; A represents a single bond or a methylene group; and $R^5$ represents a substituted or unsubstituted phenyl group; and a transition metal complex comprising the 1-substituted-2-diphenylphosphinonaphthalene as a ligand. The transition metal complex is useful as a catalyst in asymmetric synthesis.

3 Claims, No Drawings

1-SUBSTITUTED-2-DIPHENYLPHOSPHINONAPHTHALENE AND TRANSITION METAL COMPLEX COMPRISING THE SAME AS A LIGAND

BACKGROUND OF THE INVENTION

This invention relates to a novel 1-substituted-2-diphenylphosphinonaphthalene which is capable of forming a complex with a transition metal, such as ruthenium, palladium or rhodium, to provide a catalyst for various asymmetric synthesis reactions.

BACKGROUND OF THE INVENTION

A great number of reports have been made on transition metal complexes for use as a catalyst for organic syntheses, such as asymmetric hydrogenation, asymmetric isomerization, asymmetric hydrosilylation, and asymmetric allylation.

As for complexes comprising a transition metal, e.g., rhodium, palladium or ruthenium, and an optically active tertiary phosphine compound as a ligand, various phosphine compounds having a special structure have been developed to impart further improved catalyst activity in asymmetric synthesis as disclosed, e.g., in The Chemical Society of Japan (ed.), KAGAKU SOSETSU, Vol. 32, pp. 235–241, "YUKI KINZOKU SAKUTAI NO KAGAKU" (1982) and Ryoji Noyori, *Asymmetric Catalysis in Organic Synthesis*, A Wiley-Interscience Publication.

In particular, 2,2'-bis(diphenylphosphino)-1,1'-binaphthyl (hereinafter abbreviated as BINAP) is one of the excellent phosphine ligands so far proposed, which has provided a rhodium complex (JP-A-55-61937, the term "JP-A" as used herein means an "unexamined published Japanese patent application") and a ruthenium complex (JP-A-61-63690). A palladium complex comprising a 2-substituted-2'-diphenylphosphino-1,1'-binaphthyl as a ligand (JP-A-5-17491) has also been reported.

On the other hand, known mononaphthalene type ligands include diphenyl-(1-substituted-2-naphthyl)phosphine compounds represented by formula (II) (JP-A-6-256367) or formula (III) shown below (Synthesis, pp. 199–202 (January, 1994)).

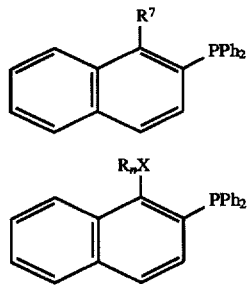

wherein $R^7$ represents an alkyl group having 1 to 20 carbon atoms, an aralkyl group, an aryl group, an alkoxy group, an oxyaralkyl group, an alkylamino group, or an aralkylamino group; and Ph represents a phenyl group or a substituted phenyl group.

Under the present situation, it has been demanded to develop a novel catalyst that can be applied to various reactions or various reaction substrates.

SUMMARY OF THE INVENTION

An object of the present invention is to provide a catalyst for various asymmetric synthesis reactions which is excellent in substrate selectivity and conversion and has a long duration of activity.

In the light of the above-mentioned circumstances the inventors of the present invention extensively researched on many phosphine compounds and found as a result that a transition metal complex having, as a ligand, a 2-diphenylphosphinonaphthalene compound having introduced into the 1-position thereof a pyrrolidinyl group exhibits marked selectivity in asymmetric synthesis. The invention has been completed based on this finding.

The invention provides a 1-substituted-2-diphenylphosphinonaphthalene represented by formula (I):

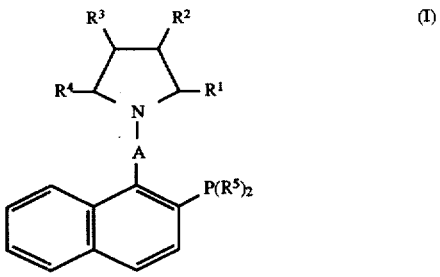

wherein at least one of $R^1$, $R^2$, $R^3$, and $R^4$, which may be the same or different, represents a lower alkyl group having 1 to 4 carbon atoms which may be substituted with an alkoxy group, a phenyl group or —$OR^6$ (wherein $R^6$ represents a hydrogen atom, a lower alkyl group having 1 to 4 carbon atoms or an alcohol-protective group), and the rest of them represent a hydrogen atom; A represents a single bond or a methylene group; and $R^5$ represents a substituted or unsubstituted phenyl group.

The invention also provides a transition metal complex comprising the 1-substituted-2-diphenylphosphinonaphthalene of formula (I) as a ligand.

DETAILED DESCRIPTION OF THE INVENTION

In formula (I), the lower alkyl group having 1 to 4 carbon atoms includes methyl, ethyl, propyl, isopropyl, butyl, sec-butyl, and t-butyl groups. Methyl, ethyl and isopropyl groups are preferred.

The lower alkyl group may be substituted with an alkoxy group, such as an alkoxy group having 1 to 4 carbon atoms, e.g., methoxy, ethoxy, propoxy, butoxy, and t-butyloxy groups.

Examples of the alkoxy-substituted alkyl group are methoxymethyl, ethoxymethyl, propoxymethyl, butoxymethyl, t-butyloxymethyl, 2-methoxyethyl, 2-ethoxyethyl, 2-propoxyethyl, 2-butoxyethyl, 2-t-butyloxyethyl, 3-methoxypropyl, 3-ethoxypropyl, 3-butoxypropyl, and 4-methoxybutyl, with methoxymethyl being preferred.

$R^6$ in —$OR^6$ as $R^1$, $R^2$, $R^3$ or $R^4$ is a hydrogen atom, a lower alkyl group having 1 to 4 carbon atoms or an alcohol-protective group. Examples of the lower alkyl group having 1 to 4 carbon atoms are the same as those described above. The alcohol-protective group is not particularly limited and includes a tri(lower alkyl)silyl group (e.g., t-butyldimethylsilyl), a diphenyl(lower alkyl)silyl group, a triphenylsilyl group, a lower alkylcarbonyl group, a t-butoxycarbonyl group, a thexyl group, a benzyl group, and a benzoyl group, with a t-butyldimethylsilyl group and a benzyl group being preferred. Examples of the lower alkyl moiety of these alcohol-protective groups are the same as those enumerated above.

$R^5$ represents a substituted or unsubstituted phenyl group. The substituent of the substituted phenyl group includes a halogen atom, e.g., fluorine, chlorine, bromine or iodine, the above-described lower alkyl group having 1 to 4 carbon atoms, and the above-described alkoxy group having 1 to 4 carbon atoms.

Examples of the substituted phenyl group are p-fluorophenyl, m-fluorophenyl, p-chlorophenyl, m-chlorophenyl, p-bromophenyl, m-bromophenyl, p-iodophenyl, m-iodophenyl, p-tolyl, m-tolyl, 3,5-dimethylphenyl, p-ethylphenyl, m-ethylphenyl, 3,5-diethylphenyl, p-isopropylphenyl, m-isopropylphenyl, 3,5-diisopropylphenyl, p-t-butylphenyl, p-methoxyphenyl, m-methoxyphenyl, 3,5-dimethoxyphenyl, p-ethoxyphenyl, p-propoxyphenyl, and p-butoxyphenyl. Preferred of them is p-tolyl.

Specific but non-limiting examples of the 1-substituted-2-diphenylphosphinonaphthalene compounds represented by formula (I) are shown in Tables 1 to 14 below. In the Tables, abbreviations have the following meaning.

Me=Methyl group
Et=Ethyl group
Pr=Propyl group
iPr=Isopropyl group
Bu=Butyl group
sec-Bu=sec-Butyl group
tert-Bu=t-Butyl group
Ph=Phenyl group
OTBDMS=t-Butyldimethylsilyloxy group.

TABLE 1

| $R^1$ | $R^2$ | $R^3$ | $R^4$ | A | $R^5$ |
| --- | --- | --- | --- | --- | --- |
| Me | H | H | Me | single bond | Ph |
| Me | H | H | Me | methylene | Ph |
| H | Ph | Ph | H | single bond | Ph |
| Me | H | H | H | single bond | Ph |
| iPr | H | H | H | single bond | Ph |
| —CH₂OMe | H | H | H | single bond | Ph |
| Et | H | H | H | single bond | Ph |
| Pr | H | H | H | single bond | Ph |
| Bu | H | H | H | single bond | Ph |
| sec-Bu | H | H | H | single bond | Ph |
| tert-Bu | H | H | H | single bond | Ph |
| —CH₂OEt | H | H | H | single bond | Ph |
| —CH₂OPr | H | H | H | single bond | Ph |
| —CH₂OiPr | H | H | H | single bond | Ph |
| —CH₂OBu | H | H | H | single bond | Ph |
| —CH₂Otert-Bu | H | H | H | single bond | Ph |
| Ph | H | H | H | single bond | Ph |
| OH | H | H | H | single bond | Ph |
| OMe | H | H | H | single bond | Ph |
| OTBDMS | H | H | H | single bond | Ph |

TABLE 2

| $R^1$ | $R^2$ | $R^3$ | $R^4$ | A | $R^5$ |
| --- | --- | --- | --- | --- | --- |
| H | Me | H | H | single bond | Ph |
| H | iPr | H | H | single bond | Ph |
| H | Et | H | H | single bond | Ph |
| H | Pr | H | H | single bond | Ph |
| H | Bu | H | H | single bond | Ph |
| H | sec-Bu | H | H | single bond | Ph |
| H | tert-Bu | H | H | single bond | Ph |
| H | Ph | H | H | single bond | Ph |
| H | OH | H | H | single bond | Ph |
| H | OMe | H | H | single bond | Ph |

TABLE 2-continued

| $R^1$ | $R^2$ | $R^3$ | $R^4$ | A | $R^5$ |
| --- | --- | --- | --- | --- | --- |
| H | OTBDMS | H | H | single bond | Ph |
| Et | H | H | Et | single bond | Ph |
| Pr | H | H | Pr | single bond | Ph |
| iPr | H | H | iPr | single bond | Ph |
| Bu | H | H | Bu | single bond | Ph |
| —CH₂OMe | H | H | —CH₂OMe | single bond | Ph |
| —CH₂OEt | H | H | —CH₂OEt | single bond | Ph |
| —CH₂OPr | H | H | —CH₂OPr | single bond | Ph |
| —CH₂OBu | H | H | —CH₂OBu | single bond | Ph |
| Ph | H | H | Ph | single bond | Ph |

TABLE 3

| $R^1$ | $R^2$ | $R^3$ | $R^4$ | A | $R^5$ |
| --- | --- | --- | --- | --- | --- |
| H | Me | Me | H | single bond | Ph |
| H | Et | Et | H | single bond | Ph |
| H | iPr | iPr | H | single bond | Ph |
| H | Bu | Bu | H | single bond | Ph |
| H | OH | OH | H | single bond | Ph |
| H | OMe | OMe | H | single bond | Ph |
| H | OTBDMS | OTBDMS | H | single bond | Ph |
| H | OH | H | Me | single bond | Ph |
| H | OMe | H | Me | single bond | Ph |
| H | OTBDMS | H | Me | single bond | Ph |
| H | OCH₂Ph | H | Me | single bond | Ph |
| H | OH | H | —CH₂OMe | single bond | Ph |
| H | OMe | H | —CH₂OMe | single bond | Ph |
| H | OTBDMS | H | —CH₂OMe | single bond | Ph |
| H | OCH₂Ph | H | —CH₂OMe | single bond | Ph |

TABLE 4

| $R^1$ | $R^2$ | $R^3$ | $R^4$ | A | $R^5$ |
| --- | --- | --- | --- | --- | --- |
| Me | H | H | H | methylene | Ph |
| iPr | H | H | H | methylene | Ph |
| —CH₂OMe | H | H | H | methylene | Ph |
| Et | H | H | H | methylene | Ph |
| Pr | H | H | H | methylene | Ph |
| Bu | H | H | H | methylene | Ph |
| sec-Bu | H | H | H | methylene | Ph |
| tert-Bu | H | H | H | methylene | Ph |
| —CH₂OEt | H | H | H | methylene | Ph |
| —CH₂OPr | H | H | H | methylene | Ph |
| —CH₂OiPr | H | H | H | methylene | Ph |
| —CH₂OBu | H | H | H | methylene | Ph |
| —CH₂Otert-Bu | H | H | H | methylene | Ph |
| Ph | H | H | H | methylene | Ph |
| OH | H | H | H | methylene | Ph |
| OMe | H | H | H | methylene | Ph |
| OTBDMS | H | H | H | methylene | Ph |

TABLE 5

| $R^1$ | $R^2$ | $R^3$ | $R^4$ | A | $R^5$ |
| --- | --- | --- | --- | --- | --- |
| H | Me | H | H | methylene | Ph |
| H | iPr | H | H | methylene | Ph |
| H | Et | H | H | methylene | Ph |
| H | Pr | H | H | methylene | Ph |
| H | Bu | H | H | methylene | Ph |
| H | sec-Bu | H | H | methylene | Ph |
| H | tert-Bu | H | H | methylene | Ph |
| H | Ph | H | H | methylene | Ph |
| H | OH | H | H | methylene | Ph |
| H | OMe | H | H | methylene | Ph |
| H | OTBDMS | H | H | methylene | Ph |
| Et | H | H | Et | methylene | Ph |
| Pr | H | H | Pr | methylene | Ph |

TABLE 5-continued

| R¹ | R² | R³ | R⁴ | A | R⁵ |
|---|---|---|---|---|---|
| iPr | H | H | iPr | methylene | Ph |
| Bu | H | H | Bu | methylene | Ph |
| —CH₂OMe | H | H | —CH₂OMe | methylene | Ph |
| —CH₂OEt | H | H | —CH₂OEt | methylene | Ph |
| —CH₂OPr | H | H | —CH₂OPr | methylene | Ph |
| —CH₂OBu | H | H | —CH₂OBu | methylene | Ph |
| Ph | H | H | Ph | methylene | Ph |

TABLE 6

| R¹ | R² | R³ | R⁴ | A | R⁵ |
|---|---|---|---|---|---|
| H | Me | Me | H | methylene | Ph |
| H | Et | Et | H | methylene | Ph |
| H | iPr | iPr | H | methylene | Ph |
| H | Bu | Bu | H | methylene | Ph |
| H | OH | OH | H | methylene | Ph |
| H | OMe | OMe | H | methylene | Ph |
| H | OTBDMS | OTBDMS | H | methylene | Ph |
| H | Ph | Ph | H | methylene | Ph |
| H | OH | H | Me | methylene | Ph |
| H | OMe | H | Me | methylene | Ph |
| H | OTBDMS | H | Me | methylene | Ph |
| H | OCH₂Ph | H | Me | methylene | Ph |
| H | OH | H | —CH₂OMe | methylene | Ph |
| H | OMe | H | —CH₂OMe | methylene | Ph |
| H | OTBDMS | H | —CH₂OMe | methylene | Ph |
| H | OCH₂Ph | H | —CH₂OMe | methylene | Ph |

TABLE 7

| R¹ | R² | R³ | R⁴ | A | R⁵ |
|---|---|---|---|---|---|
| Me | H | H | Me | single bond | p-tolyl |
| Me | H | H | Me | methylene | p-tolyl |
| H | Ph | Ph | H | single bond | p-tolyl |
| Me | H | H | H | single bond | p-tolyl |
| iPr | H | H | H | single bond | p-tolyl |
| —CH₂OMe | H | H | H | single bond | p-tolyl |
| Et | H | H | H | single bond | p-tolyl |
| Pr | H | H | H | single bond | p-tolyl |
| Bu | H | H | H | single bond | p-tolyl |
| sec-Bu | H | H | H | single bond | p-tolyl |
| tert-Bu | H | H | H | single bond | p-tolyl |
| —CH₂OEt | H | H | H | single bond | m-tolyl |
| —CH₂OPr | H | H | H | single bond | m-tolyl |
| —CH₂OiPr | H | H | H | single bond | m-tolyl |
| —CH₂OBu | H | H | H | single bond | m-tolyl |
| —CH₂Otert-Bu | H | H | H | single bond | m-tolyl |
| Ph | H | H | H | single bond | m-tolyl |
| OH | H | H | H | single bond | m-tolyl |
| OMe | H | H | H | single bond | m-tolyl |
| OTBDMS | H | H | H | single bond | m-tolyl |

TABLE 8

| R¹ | R² | R³ | R⁴ | A | R⁵ |
|---|---|---|---|---|---|
| H | Me | H | H | single bond | 3,5-dimethyl-phenyl |
| H | iPr | H | H | single bond | 3,5-dimethyl-phenyl |
| H | —CH₂OMe | H | H | single bond | 3,5-dimethyl-phenyl |
| H | Et | H | H | single bond | 3,5-dimethyl-phenyl |
| H | Pr | H | H | single bond | 3,5-dimethyl-phenyl |
| H | Bu | H | H | single bond | 3,5-dimethyl-phenyl |

TABLE 8-continued

| R¹ | R² | R³ | R⁴ | A | R⁵ |
|---|---|---|---|---|---|
| H | sec-Bu | H | H | single bond | 3,5-dimethyl-phenyl |
| H | tert-Bu | H | H | single bond | 3,5-dimethyl-phenyl |
| H | Ph | H | H | single bond | 3,5-dimethyl-phenyl |

TABLE 9

| R¹ | R² | R³ | R⁴ | A | R⁵ |
|---|---|---|---|---|---|
| H | Me | H | H | single bond | p-methoxy-phenyl |
| H | iPr | H | H | single bond | p-methoxy-phenyl |
| H | Et | H | H | single bond | p-methoxy-phenyl |
| H | Pr | H | H | single bond | p-methoxy-phenyl |
| H | Bu | H | H | single bond | p-methoxy-phenyl |
| Et | H | H | Et | single bond | p-chloro-phenyl |
| Pr | H | H | Pr | single bond | p-chloro-phenyl |
| iPr | H | H | iPr | single bond | p-chloro-phenyl |
| Bu | H | H | Bu | single bond | p-chloro-phenyl |
| —CH₂OMe | H | H | —CH₂OMe | single bond | p-chloro-phenyl |
| —CH₂OEt | H | H | —CH₂OEt | single bond | p-chloro-phenyl |

TABLE 10

| R¹ | R² | R³ | R⁴ | A | R⁵ |
|---|---|---|---|---|---|
| —CH₂OPr | H | H | —CH₂OPr | single bond | p-chloro-phenyl |
| —CH₂OBu | H | H | —CH₂OBu | single bond | p-chloro-phenyl |
| Ph | H | H | Ph | single bond | p-chloro-phenyl |
| H | Me | Me | H | single bond | m-chloro-phenyl |
| H | Et | Et | H | single bond | m-chloro-phenyl |
| H | iPr | iPr | H | single bond | m-chloro-phenyl |
| H | Bu | Bu | H | single bond | m-chloro-phenyl |
| H | OH | OH | H | single bond | m-chloro-phenyl |
| H | OMe | OMe | H | single bond | m-chloro-phenyl |
| H | OTBDMS | OTBDMS | H | single bond | m-chloro-phenyl |
| H | OCH₂Ph | OCH₂Ph | H | single bond | m-chloro-phenyl |

TABLE 11

| R¹ | R² | R³ | R⁴ | A | R⁵ |
|---|---|---|---|---|---|
| H | OH | H | Me | single bond | p-tolyl |
| H | OMe | H | Me | single bond | p-tolyl |
| H | OTBDMS | H | Me | single bond | p-tolyl |
| H | OCH₂Ph | H | Me | single bond | p-tolyl |
| H | OH | H | —CH₂OMe | single bond | p-tolyl |

TABLE 11-continued

| R¹ | R² | R³ | R⁴ | A | R⁵ |
|---|---|---|---|---|---|
| H | OMe | H | —CH₂OMe | single bond | p-tolyl |
| H | OTBDMS | H | —CH₂OMe | single bond | p-tolyl |
| H | OCH₂Ph | H | —CH₂OMe | single bond | p-tolyl |
| Me | H | H | H | methylene | p-tolyl |
| iPr | H | H | H | methylene | p-tolyl |
| —CH₂OMe | H | H | H | methylene | p-tolyl |
| Et | H | H | H | methylene | p-tolyl |
| Pr | H | H | H | methylene | p-tolyl |
| Bu | H | H | H | methylene | p-tolyl |
| sec-Bu | H | H | H | methylene | p-tolyl |
| tert-Bu | H | H | H | methylene | m-tolyl |
| —CH₂OEt | H | H | H | methylene | m-tolyl |
| —CH₂OPr | H | H | H | methylene | m-tolyl |
| Ph | H | H | H | methylene | m-tolyl |
| OHH | H | H | H | methylene | m-tolyl |
| OMe | H | H | H | methylene | m-tolyl |
| OTBDMS | H | H | H | methylene | m-tolyl |

TABLE 12

| R¹ | R² | R³ | R⁴ | A | R⁵ |
|---|---|---|---|---|---|
| H | Me | H | H | methylene | 3,5-dimethyl-phenyl |
| H | iPr | H | H | methylene | 3,5-dimethyl-phenyl |
| H | —CH₂OMe | H | H | methylene | 3,5-dimethyl-phenyl |
| H | Et | H | H | methylene | 3,5-dimethyl-phenyl |
| H | Pr | H | H | methylene | 3,5-dimethyl-phenyl |
| H | Bu | H | H | methylene | 3,5-dimethyl-phenyl |
| H | Ph | H | H | methylene | 3,5-dimethyl-phenyl |

TABLE 13

| R¹ | R² | R³ | R⁴ | A | R⁵ |
|---|---|---|---|---|---|
| Et | H | H | Et | methylene | p-chloro-phenyl |
| Pr | H | H | Pr | methylene | p-chloro-phenyl |
| iPr | H | H | iPr | methylene | p-chloro-phenyl |
| Bu | H | H | Bu | methylene | p-chloro-phenyl |
| —CH₂OMe | H | H | —CH₂OMe | methylene | p-chloro-phenyl |
| —CH₂OEt | H | H | —CH₂OEt | methylene | p-chloro-phenyl |
| Ph | H | H | Ph | methylene | p-chloro-phenyl |
| H | Me | Me | H | methylene | m-chloro-phenyl |
| H | Et | Et | H | methylene | m-chloro-phenyl |
| H | iPr | iPr | H | methylene | m-chloro-phenyl |

TABLE 14

| R¹ | R² | R³ | R⁴ | A | R⁵ |
|---|---|---|---|---|---|
| H | Bu | Bu | H | methylene | m-chloro-phenyl |
| H | OH | OH | H | methylene | m-chloro-phenyl |

TABLE 14-continued

| R¹ | R² | R³ | R⁴ | A | R⁵ |
|---|---|---|---|---|---|
| H | OMe | OMe | H | methylene | m-chloro-phenyl |
| H | OTBDMS | OTBDMS | H | methylene | m-chloro-phenyl |
| H | OH | H | Me | methylene | p-tolyl |
| H | OMe | H | Me | methylene | p-tolyl |
| H | OTBDMS | H | Me | methylene | p-tolyl |
| H | OCH₂Ph | H | Me | methylene | p-tolyl |
| H | OH | H | —CH₂OMe | methylene | p-tolyl |
| H | OMe | H | —CH₂OMe | methylene | p-tolyl |
| H | OTBDMS | H | —CH₂OMe | methylene | p-tolyl |
| H | OCH₂Ph | H | —CH₂OMe | methylene | p-tolyl |

The 1-substituted-2-diphenylphosphinonaphthalene of formula (I) contains as many asymmetric carbon atoms as the substituents represented by $R^1$, $R^2$, $R^3$, and $R^4$. For example, where only one of them is a substituent ($\neq H$), there would be (R) and (S) optical isomers. Where two of them are substituents, there would be (R,R), (R,S), (S,R) and (S,S) optical isomers. All of these isomers are included in formula (I).

Where the 1-substituted-2-diphenylphosphinonaphthalene has one substituent on its pyrrolidine ring, the substituent is preferably at the 2-position of the pyrrolidine ring. Where the pyrrolidine ring has two substituents, the compound of formula (I) preferably includes those represented by formula (IA), (IB) or (IC):

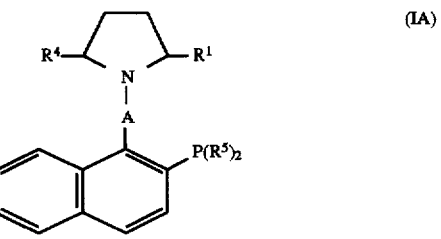

(IA)

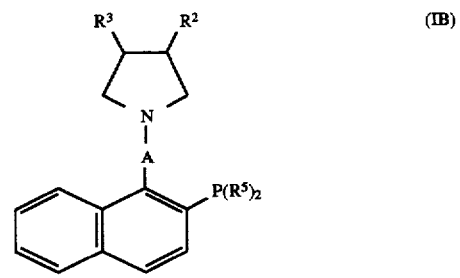

(IB)

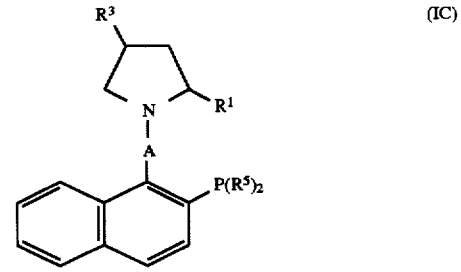

(IC)

wherein $R^1$, $R^2$, $R^3$, $R^4$, $R^5$, and A are as defined above.

Of the compounds of formula (I), those represented by formula (VI), which corresponds to formula (IA) wherein A is a single bond, are prepared according to the following reaction formula:

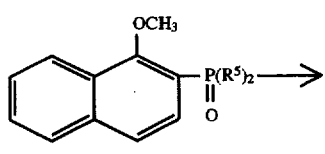

(IV)

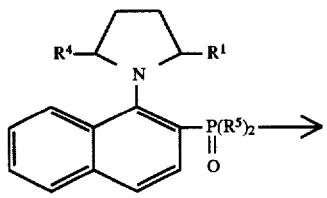

(V)

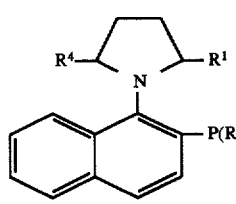

(VI)

wherein $R^1$, $R^4$, and Ph are as defined above.

That is, 1-methoxy-2-diphenylphosphinonaphthalene (IV) and a 2,5-disubstituted pyrrolidine are reacted to provide a 1-(2,5-disubstituted pyrrolidinyl)-2-diphenylphosphinylnaphthalene (V), which is then reduced with trichlorosilane to give a 1-(2,5-disubstituted pyridinyl)-2-diphenylphosphinonaphthalene (VI).

Those represented by formula (XI), which corresponds to formula (IA) with A being a methylene group, are prepared, for example, in accordance with the following reaction formula:

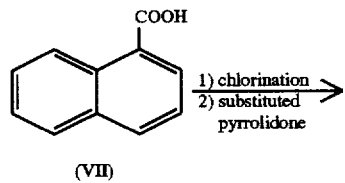

(VII)

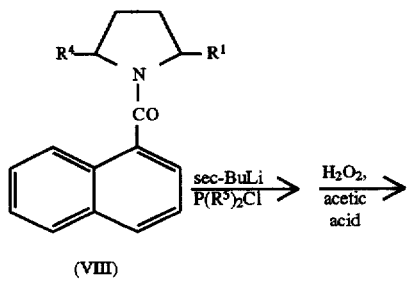

(VIII)

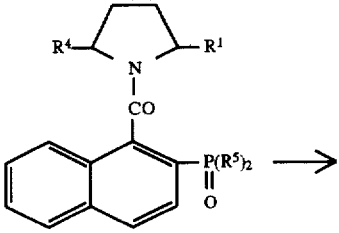

(IX)

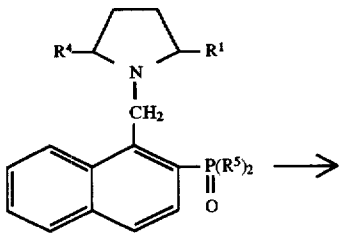

(X)

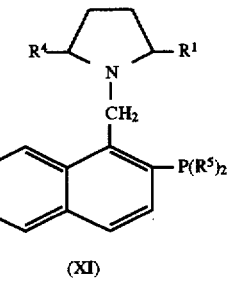

(XI)

wherein $R^1$, $R^4$, and $R^5$ are as defined above.

That is, 1-naphthoic acid (VII) is chlorinated and reacted with a 2,5-disubstituted pyrrolidine to obtain an N-(1-naphthoyl)-2,5-disubstituted pyrrolidine (VIII), which is then reacted with sec-butyl lithium in the presence of N,N,N',N'-tetramethylethylenediamine to introduce lithium to the o-position. The resulting lithium compound is then reacted with chlorodiphenylphosphine, and the reaction product is reacted with hydrogen peroxide in the presence of acetic acid to obtain a 1-(2,5-disubstituted pyrrolidinylamido)-2-diphenylphosphinylnaphthalene (IX). The compound (IX) is reduced with a reducing agent, such as sodium borohydride, to obtain a 1-(2,5-disubstituted pyrrolidinylmethyl)-2-diphenylphosphinylnaphthalene (X), which is reduced with trichlorosilane to give a 1-(2,5-disubstituted pyrrolidinylmethyl)-2-diphenylphosphinonaphthalene (XI).

Other compounds of formula (I) in which the substituted pyrrolidine ring is different from that of the compounds (VI) or (XI) in position and number of its substituents can be obtained by starting with the corresponding substituted pyrrolidine compound in place of the 2,5-disubstituted pyrrolidine compound.

The 1-substituted-2-diphenylphosphinonaphthalene of formula (I) according to the invention serves as a ligand to form a transition metal complex on reacting with a transition metal compound. The transition metal forming the complex includes the metals of the Groups 8–10 using the IUPAC new notation (corresponding to the former group VIII) of the Periodic Table, such as palladium, ruthenium, and rhodium.

Of the transition metal complexes of the invention, palladium complexes, for instance, can easily be obtained by reacting the 1-substituted-2-diphenylphosphinonaphthalene of formula (I) with a palladium compound in accordance with a known process described, e.g., in The Chemical Society of Japan (ed.), *Jikken Kagaku Koza*, (4th Ed.), Vol. 18, "Yuki Kinzoku Sakutai", pp. 391–411, Maruzen (1991).

While not limiting, divalent or monovalent palladium compounds are used mostly. Examples of usable palladium compounds are PdCl₂(PhCN)₂, Pd(cod)Cl₂ (wherein cod stands for 1,5-cyclooctadiene), PdCl₂(CH₃CN)₂, Na₂PdCl₄, Pd(dba)₂ (wherein dba stands for dibenzylideneacetone), Pd(OC(O)CH₃)₂, Pd(acac)₂ (wherein acac represents acetylacetonato), [Pd(η-C₃H₅)(cod)]⁺BF₄⁻, and Pd(η-C₃H₅)[C₅(CH₃)₅]. In particular, PdCl₂(PhCN)₂, [Pd(η-C₃H₅)(cod)]⁺BF₄⁻, and Pd(η-C₃H₅)[C₅(CH₃)₅] are preferred.

In more detail, palladium complexes can be prepared according to the following reaction formulae, in which L represents a 1-substituted-2-diphenylphosphinonaphthalene of formula (I).

PdCl₂(PhCN)₂+2L→PdCl₂(L)₂+2PhCN

Pd(cod)Cl₂+2L→PdCl₂(L)₂+2cod

PdCl₂(CH₃CN)₂+2L→PdCl₂(L)₂+2CH₃CN

[Pd(η-C₃H₅)(cod)]⁺BF₄⁻+L→[(η-C₃H₅)Pd(L)]⁺BF₄⁻

[Pd(η-C₃H₅)PdCl]₂+2L→2[(η-C₃H₅)PdCl(L)]

Specific examples of the thus prepared palladium complexes include PdCl₂(L)₂, [(η-C₃H₅)Pd(L)]⁺BF₄⁻, [(η-C₃H₅)Pd(L)]PF₆, and [(η-C₃H₅)PdCl(L)], with [(η-C₃H₅)Pd(L)]⁺BF₄⁻, [(η-C₃H₅)Pd(L)]PF₆, and [(η-C₃H₅)PdCl(L)] being particularly preferred.

Ruthenium complexes and rhodium complexes according to the invention are also obtained easily by reacting a ruthenium compound or a rhodium compound and the compound of formula (I) in accordance with the known process described in The Chemical Society of Japan (ed.), *Jikken Kagaku Koza*, (4th Ed.), Vol. 18, "Yuki Kinzoku Sakutai", pp. 254–284 and pp. 327–353, respectively, Maruzen (1991).

Specific examples of useful ruthenium compounds and rhodium compounds are RuCl₃.3H₂O, [Ru(cod)Cl₂]₂, [RuCl₂(η-C₆H₆)]₂, [RuCl₂(η-hexamethylbenzene)]₂, Ru(η-C₃H₅)(nbd) (wherein nbd represents norbornadiene), [(cod)RhCl]₂, [(nbd)RhCl]₂, [(cod)Rh)]⁺ClO₄⁻, and [(nbd)Rh]⁺BF₄⁻.

More specifically, ruthenium complexes and rhodium complexes can be prepared according to the following reaction formulae:

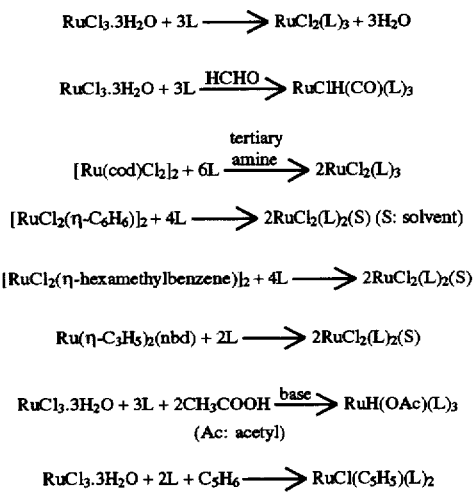

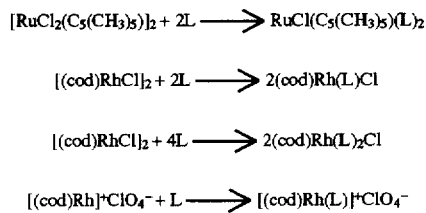

The solvent S used above includes methylene chloride, chloroform, tetrahydrofuran, acetonitrile, benzonitrile, dimethylformamide, and dimethyl sulfoxide.

Specific examples of the thus prepared ruthenium complexes and rhodium complexes are RuCl₂(L)₃, RuClH(CO)(L)₃, RuCl₂(L)₂(S), RuH(OAc)(L)₃, RuCl(C₅H₅)(L)₂, RuCl(C₅(CH₃)₅)(L)₂, RuI₂(p-cymene)(L)₂, (cod)RuCl(L)₂, [Rh(cod)(L)₂]⁺ClO₄⁻, [Rh(cod)(L)₂]⁺BF₄⁻, and [Rh(nbd)(L)₂]⁺ClO₄⁻. In particular, RuCl₂(L)₃ and RuI₂(p-cymene)(L)₂ are preferred of them.

The transition metal complex according to the invention catalyzes asymmetric synthesis, for example, asymmetric allylation illustrated by the following reaction formula to afford a desired compound in a high yield.

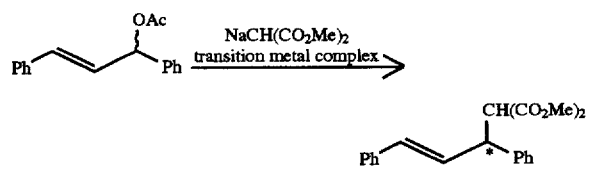

wherein Ac represents an acetyl group; Ph represents a phenyl group; Me represents a methyl group; and * indicates an asymmetric carbon atom.

The above reaction can be carried out by adding a transition metal compound and a 1-substituted-2-diphenylphosphinonaphthalene of formula (I) separately to the reaction system instead of using a previously prepared transition metal complex.

As described above, the transition metal complex obtained from the 1-substituted-2-diphenylphosphinonaphthalene of formula (I) according to the present invention is useful as a catalyst of asymmetric synthesis, for example, asymmetric allylation to provide a desired product in a high yield. An appropriate selection of the optical isomerism of the compound of formula (I) to be used as a ligand of the transition metal complex will result in production of the asymmetric reaction product with a desired absolute configuration.

The present invention will now be illustrated in greater detail with reference to Examples and Application Examples, but it should be understood that the invention is not construed as being limited thereto.

Measurement of data in Examples was made with the following instruments.

High performance liquid chromatography (HPLC): LC-4A (manufactured by Shimadzu Corp.)

³¹P-NMR: AM-400 (manufactured by Bruker JAPAN Co., LTD.)

Specific rotation: JASCO DIP-1000, Union Giken PM-101

Elementary analysis: YANAKO MT-5 CHN CORDER

EXAMPLE 1

Synthesis of 1-((2R,5R)-2,5-Dimethylpyrrolidinyl)-2-diphenylphosphinonaphthalene (Ia)

1) In a 300 ml four-necked flask was charged 1.1 g (11 mmol) of (2R,5R)-2,5-dimethylpyrrolidine in a nitrogen stream, and 70 ml of tetrahydrofuran (THF) was added thereto. To the flask was added dropwise 7.7 ml (13.2 mmol) of butyl lithium at −78° C. (methanol-dry ice) over 10 minutes. After maintaining the system at that temperature for 10 minutes, the mixture was stirred at 0° C. for 1 hour to prepare lithium amide. In a separate container 4 g (11 mmol) of 1-methoxy-2-diphenylphosphinylnaphthalene was dissolved in 35 ml of THF, and the lithium amide was slowly added dropwise to the resulting solution cooled to −20° C. (carbon tetrachloride-dry ice), followed by allowing the mixture to react for 4 hours. The reaction was stopped by addition of a saturated sodium chloride aqueous solution, and the reaction mixture was extracted with ethyl ether. The extract was washed with water and dried over anhydrous magnesium sulfate. The resulting crude product was purified by silica gel column chromatography using a 1/1 (by volume) mixture of hexane and acetone as an eluent to give 3.24 g of 1-((2R,5R)-2,5-dimethylpyrrolidinyl)-2-diphenylphosphinylnaphthalene in a yield of 69%.

2) To a solution of 3.3 g (7.8 mmol) of the 1-((2R,5R)-2,5-dimethylpyrrolidinyl)-2-diphenylphosphinylnaphthalene in 100 ml of xylene were added 6.8 ml (49.14 mmol) of triethylamine and 4.7 ml (46.8 mmol) of trichlorosilane, and the mixture was slowly heated up to 120° C., at which the mixture was stirred for 6.5 hours. After cooling to room temperature, the reaction mixture was poured into 250 ml of 2N NaOH and extracted with benzene. The extract was washed with water and dried over anhydrous magnesium sulfate. The crude product was purified by silica gel column chromatography (hexane/acetone=20/1 by volume) to give 2.71 g of the title compound in a yield of 85%.

$^1$H-NMR (250 MHz, CDCl$_3$, δ ppm): 0.78 (d, 3H, J=6.1 Hz, —CH$_3$), 0.87 (d, 3H, J=6.1 Hz, —CH$_3$), 1.59–1.80 (m, 2H), 2.18–2.36 (m, 2H, —CH$_2$–CH$_2$), 4.16–4.42 (m, 2H, —N—CH), 7.16–7.49 (m, 16H, Ar) IR (KBr) ν (cm$^{-1}$): 3050, 2820, 1578, 1549, 1430, 1384, 1348, 1255, 1162, 1088, 1023, 814, 743, 693 Melting point: 150.7°–150.9° C. $[α]_D^{15.2}$=+287.7° (c=0.978, CHCl$_3$) Elementary analysis for C$_{28}$H$_{28}$NP: Calcd. (%): C 82.12; H 6.89; N 3.42 Found (%): C 82.01; H 7.12; N 3.65

EXAMPLE 2

Synthesis of 1-((2R,5R)-2,5-Dimethylpyrrolidinylmethyl)-2-diphenylphosphinonaphthalene (Ib)

1) N-(1-Naphthoyl)-(2R,5R)-2,5-dimethylpyrrolidine:

In a flask were charged 0.73 g of 1-naphthoic acid and 3 ml of thionyl chloride and stirred at 80° C. for 3 hours. After allowing the mixture to cool, the excess thionyl chloride was removed. The reaction mixture was dried under reduced pressure, and 3 ml of anhydrous benzene, 0.5 ml of pyridine, and 350 mg of (2R,5R)-2,5-dimethylpyrrolidine were added thereto. The mixture was allowed to react at room temperature for 5 hours and then under reflux for 2 hours. 2N HCl was added to stop the reaction. The reaction mixture was extracted with ethyl ether and washed successively with 2N sodium carbonate and water. The crude product was purified by silica gel column chromatography to give 543.7 mg (61%) of the title compound.

2) 1-((2R,5R)-2,5-Dimethylpyrrolidinylamido)-2-diphenylphosphinylnaphthalene:

A 50 ml two-necked eggplant flask containing 355.4 mg of N-(1-naphthoyl)-(2R,5R)-2,5-dimethylpyrrolidine was purged with nitrogen, and THF and 0.2 ml of tetramethylethylenediamine were added to the flask, followed by stirring. After cooling to −78° C., sec-butyl lithium was slowly added thereto dropwise, followed by stirring for 1 hour. Chlorodiphenylphosphine was slowly added dropwise at −78° C., and the mixture was stirred for 0.5 hour. The reaction was stopped by addition of 2N HCl. An attempt to extract the reaction mixture with ethyl ether resulted in precipitation of insoluble matter. As a next attempt, the reaction mixture was extracted with chloroform. Since the aqueous layer was found turbid, it was again extracted with ethyl ether. The ethyl ether layer and the chloroform layer were combined, washed successively with 2N sodium carbonate and water, dried over anhydrous magnesium sulfate, and dried under reduced pressure.

The resulting crude product was put in a flask, 20 ml of acetic acid and 0.5 ml of 30% H$_2$O$_2$ were added thereto, and the mixture was stirred at 70° C. for 2 hours. After allowing the reaction mixture to cool, 250 ml of 2N NaOH was added at 0° C. to stop the reaction. The reaction mixture was extracted with ethyl ether, washed with water, and dried over anhydrous magnesium sulfate. The crude product was purified by silica gel column chromatography to give 461.6 mg (56%) of the title compound.

$^1$H-NMR (250 MHz, CDCl$_3$, δ ppm): 0.65 (d, 3H, J=6.6 Hz, —CH$_3$), 1.46 (d, 3H, J=6.4 Hz, —CH$_3$), 1.41–1.64 (m, 2H, —CH$_2$—), 2.02–2.17 (m, 2H, —CH$_2$—), 3.52 (pentad, 1H, N—CH), 4.37 (pentad, 1H, N—CH), 7.43–7.86 (m, 16H, Ar) IR (KBr) ν (cm$^{-1}$): 3055, 2970, 2925, 1730, 1612, 1497, 1479, 1458, 1414, 1371, 1349, 1308, 1288, 1261, 1200, 1162, 1142, 1113, 1098, 1026, 871, 851, 831, 752, 717, 694, 654, 603, 538, 512, 479 Melting point: 223.5°–225.5° C. $[α]_D^{24}$=−43.7° (c=0.998, CHCl$_3$) Elementary analysis for C$_{29}$H$_{28}$NO$_2$P: Calcd. (%): C 76.80; H 6.22; N 3.09 Found (%): C 76.92; H 6.22; N 3.08

3) 1-((2R,5R)-2,5-Dimethylpyrrolidinylmethyl)-2-diphenylphosphinylnaphthalene:

A 50 ml two-necked eggplant flask was purged with nitrogen, and 43 mg of lithium borohydride, 2 ml of anhydrous THF, and 0.5 ml of TMSCl were put therein and stirred. A solution of 447 mg of 1-((2R,5R)-2,5-dimethylpyrrolidinylamido)-2-diphenylphosphinylnaphthalene in 3 ml of anhydrous THF was added thereto, followed by refluxing for 29 hours. Methanol was carefully added thereto to cease the reaction. The reaction mixture was concentrated by means of an evaporator. 6N HCl was added to the residue, followed by heating to 100° C., and the mixture was stirred for 3 hours. The mixture was concentrated by an evaporator, and the residue was extracted with ethyl ether and washed with water. The aqueous layer was made alkaline with NaOH, extracted with ethyl ether, washed with water, and dried over anhydrous magnesium sulfate. The residue was purified by silica gel column chromatography to give 113.8 mg (26%) of the title compound.

4) 1-((2R,5R)-2,5-dimethylpyrrolidinylmethyl)-2-diphenylphosphinonaphthalene:

A two-necked eggplant flask containing 110 mg of 1-((2R,5R)-2,5-dimethylpyrrolidinylmethyl)-2-diphenylphosphinylnaphthalene was purged with nitrogen, and 8 ml of anhydrous xylene was put in and dissolved. Then, 0.22 ml of triethylamine and 0.15 ml of trichlorosilane were added thereto, and the mixture was slowly heated to 120° C. to react for 5 hours. The reaction was ceased with 2N NaOH, and the reaction mixture was extracted with ethyl ether, washed with water, and dried over anhydrous magnesium sulfate. The crude product was purified by silica gel column chromatography to obtain 27.1 mg (26%) of the title compound.

EXAMPLE 3

Synthesis of 1-((3R,4R)-3,4-Diphenylpyrrolidinyl)-2-diphenylphosphinonaphthalene (Ic)

1) The same procedure as in Example 1-(1) was followed, except for using 210.4 mg of (3R,4R)-3,4-diphenylpyrrolidine, to give 433.1 mg (84%) of 1-((3R,4R)-3,4-diphenylpyrrolidinyl)-2-diphenylphosphinylnaphthalene.

2) The resulting compound J267.8 mg) was treated in the same manner as in Example 1-(2) to give 230 mg (86%) of the title compound.

$^1$H-NMR (250 MHz, CDCl$_3$, δ ppm): 3.81 (m, 6H, alkyl), 6.99–7.91 (m, 26H, Ar) IR (KBr) ν (cm$^{-1}$): 3055, 2905, 1598, 1550, 1489, 1446, 1383, 1154, 1080, 1023, 814, 742, 693, 511 Melting point: 146.9°–148.2° C. $[α]_D^{26.2}$=−48.14° (c=1.185, CHCl$_3$) Elementary analysis for C$_{28}$H$_{28}$NP: Calcd. (%): C 82.12; H 6.89; N 3.42 Found (%): C 82.01; H 7.12; N 3.65

EXAMPLE 4

Synthesis of 1-((S)-2-Methylpyrrolidinyl)-2-diphenylphosphinonaphthalene (Id)

1) The same procedure as in Example 1-(1) was followed, except for using 0.4 ml of (S)-2-methylpyrrolidine, to obtain 530.3 mg (85%) of 1-((S)-2-methylpyrrolidinyl)-2-diphenylphosphinylnaphthalene.

2) The resulting compound (0.28 g) was treated in the same manner as in Example 1-(2) to give 225 mg (82%) of the title compound. $^1$H-NMR (250 MHz, CDCl$_3$, δ ppm):

0.80 (d, 3H, J=6.1 Hz, —CH$_3$), 1.54–1.74 (m, 1H), 1.92–2.03 (m, 2H, —CH$_2$-CH$_2$—), 2.17–2.31 (m, 1H), 3.21–3.27 (m, 2H, —N—CH$_2$), 4.15 (m, 1H, —N—CH), 7.03–8.10 (m, 16H, Ar) IR (KBr) ν (cm$^{-1}$): 2965, 2810, 1583, 1555, 1477, 1433, 1379, 1262, 1155, 1088, 1025, 820, 744, 696, 517 Melting point: 106.2°–107.5° C. $[α]_D^{10.8}$=+203.2° (c=0.806, CHCl$_3$) Elementary analysis for C$_{27}$H$_{26}$NP: Calcd. (%): C 82.00; H 6.63; N 3.54 Found (%): C 82.17; H 6.37; N 3.41

EXAMPLE 5

Synthesis of 1-((S)-2-Isopropylpyrrolidinyl)-2-diphenylphosphinonaphthalene (Ie)

1) The same procedure as in Example 1-(1) was followed, except for using 0.63 g of (S)-2-(isopropyl)pyrrolidine, to give 1.31 g (53%) of 1-((S)-2-isopropylpyrrolidinyl)-2-diphenylphosphinylnaphthalene.

2) The resulting compound (1.05 g) was treated in the same manner as in Example 1-(2) to give 0.83 g (82%) of the title compound.

$^1$H-NMR (250 MHz, CDCl$_3$, δ ppm):

0.45 (br, —CH$_3$), 0.66 (br, —CH$_3$), 0.75 (br, —CH$_3$), 0.98 (br, —CH$_3$), 1.55 (br, —CH (isopropyl)), 1.91 (br, —CH$_2$-CH$_2$—), 2.17 (br, —CH$_2$-CH$_2$—), 2.83 (br, N—CH$_2$), 3.20 (br, N—CH$_2$), 3.43 (br, N—CH$_2$), 3.62 (br, N—CH$_2$), 3.87 (br, N—CH), 4.22 (br, N—CH), 7.21–8.46 (br, Ar) Elementary analysis for C$_{29}$H$_{30}$NP: Calcd. (%): C 82.24; H 7.14; N 3.31 Found (%): C 82.22; H 6.92; N 3.27

EXAMPLE 6

Synthesis of 1-((S)-2-Methoxymethylpyrrolidinyl)-2-diphenylphosphinonaphthalene (If)

1) The same procedure as in Example 1-(1) was followed, except for using 0.39 g of (S)-2-(methoxymethyl)pyrrolidine, to give 1.15 g (93%) of 1-((S)-2-methoxymethylpyrrolidinyl)-2-diphenylphosphinylnaphthalene.

2) The resulting compound (1 g) was treated in the same manner as in Example 1-(2) to give 923.5 mg (94%) of the title compound.

IR (KBr) ν(cm$^{-1}$): 2965, 2810, 1578, 1551, 1472, 1430, 1370, 1191, 1144, 1125, 1105, 1086, 1021, 967, 935, 818, 739, 691, 498 Melting point: 112.5°–114.2° C. $[α]_D^{23.3}$=+134.9° (c=1.035, CHCl$_3$) Elementary analysis for C$_2$,H$_{28}$NP: Calcd. (%): C 79.04; H 6.63; N 3.29 Found (%): C 78.84; H 6.92; N 3.41

EXAMPLE 7

Synthesis of Allylpalladium Complex of 1-((S)-2-methylpyrrolidinyl)-2-diphenylphosphinonaphthalene (Id)

In 1 ml of dry methylene chloride, 10 mg (25 μmol) of compound (Id) synthesized in Example 4, 4.6 mg (25 μmol) of [(η$^3$—C$_3$H$_5$)PdCl]$_2$, and 5.5 mg (25 μmol) of AgBF$_4$ were dried at room temperature for 1 hour. The mixture was passed through Celite (3 cm×8 cm) to remove the precipitated AgCl, and the solvent was removed by a rotary evaporator. The residue was dried under reduced pressure to obtain the title complex [(η—C$_3$H$_5$)Pd(Id)]BF$_4$.

$^1$H-NMR (CDCl$_3$, δ ppm): 0.93 (d, J=5.3 Hz), 1.13 (d, J=5.4 Hz), 2.32–2.82 (m) 2.87–2.96 (m), 2.98–3.05 (m), 3.69–3.74 (m), 3.82–3.87 (m), 4.08–4.23 (m), 4.33–4.51 (m), 4.53–5.04 (m), 5.32–5.40 (m), 5.78–5.93 (m), 6.09–6.23 (m), 7.22–8.28 (m)

EXAMPLE 8

Synthesis of Benzeneruthenium Complex of 1-((S)-2-Methylpyrrolidinyl)-2-diphenylphosphinonaphthalene (Id)

In a Shlenk flask were charged 40 mg (0.1 mmol) of compound (Id) synthesized in Example 4, 12 mg (0.048 mmol) of [RuCl$_2$(benzene)]$_2$, 3 ml of methylene chloride, and 3 ml of ethanol, and the mixture was stirred at 50° C. in a nitrogen atmosphere for 2 hours. The solvent was removed by evaporation under reduced pressure, and the residue was dried to obtain the title complex [RuCl(benzene)(Id)$_2$]Cl.

$^{31}$P-NMR (CDCl$_3$, δ ppm): 46.77 (d, J=34 Hz), 79.41 (d, J=34 Hz)

EXAMPLE 9

Synthesis of Rhodium Complex of 1-((S)-2-Methylpyrrolidinyl)-2-diphenylphosphinonaphthalene (Id)

In a Shlenk flask were charged 40 mg (0.1 mmol) of compound (Id) synthesized in Example 4, 20 mg (0.05 mmol) of [Rh(cod)$_2$]BF$_4$, 3 ml of methylene chloride, and 3 ml of THF, and the mixture was stirred at room temperature in a nitrogen atmosphere for 2 hours. The solvent was removed by evaporation under reduced pressure, and the residue was dried to obtain the title complex [Rh(Id)$_2$]BF$_4$.

$^{31}$P-NMR (CDCl$_3$, δ ppm): 46.88 (s), 47.77 (s)

APPLICATION EXAMPLES 1 TO 15

The catalysis of the transition metal complexes according to the invention was examined in the asymmetric allylation of 1-acetoxy-1,3-diphenyl-2-propene with dimethylmalonic ester. The reaction was carried out in accordance with process A using sodium dimethylmalonate in THF or process B in which a malonate is formed in situ from dimethylmalonic eater and sodium hydride in methylene chloride.

A two-necked eggplant flask containing 0.25 g (1 mmol) of 1,3-diphenyl-2-propenyl acetate was purged with nitrogen, and 2 ml of THF was put therein. Then, 24.6 mg (0.05 mmol; corresponding to 5 mol % based on the 1,3-diphenyl-2-propenyl acetate) of [Pd(C₃H₅)Cl] and 0.15 mmol of a 1-substituted-2-diphenylphosphinonaphthalene were added thereto. An allylating agent separately prepared from sodium hydride and dimethylmalonic eater was added in an amount of 1.3 equivalents to the substrate, i.e., 1,3-diphenyl-2-propenyl acetate, to conduct reaction at room temperature for 1 to 100 hours. After completion of the reaction, the reaction was stopped by addition of a saturated ammonium chloride aqueous solution, and ethyl ether was added to the reaction mixture, followed by liquid/liquid separation. After washing two or three times with a saturated ammonium chloride aqueous solution, the organic layer was dried over anhydrous magnesium sulfate and concentrated to obtain an allylation product. The chemical yield was determined after the product was purified by silica gel column chromatography. The product was structurally identified from ¹H-NMR data (250 MHz, CDCl₃).

The ligand (L), process of allylation, palladium compound/ligand ratio ([Pd]:[L]), reaction temperature, reaction time, yield (%), and asymmetric yield (%ee) in each Application Example are shown in Table 15 below. In the Table, "r.t." stands for room temperature.

TABLE 15

| Run No. | L  | Process | [Pd]:[L] | Reaction Temp. (°C.) | Reaction Time (hr) | Yield (%) | Asymmetric Yield (% ee) |
|---------|----|---------|----------|---------------------|--------------------|-----------|-------------------------|
| 1       | Ia | A       | 2:1      | r.t.                | 24                 | 75        | 23 (S)                  |
| 2       | Ia | A       | 1:1      | r.t.                | 8                  | 98        | 28 (S)                  |
| 3       | Ia | A       | 1:2      | r.t.                | 5                  | 83        | 31 (S)                  |
| 4       | Ia | A       | 1:4      | r.t                 | 3                  | 71        | 32 (S)                  |
| 5       | Ia | A       | 1:2      | 0                   | 45                 | 79        | 39 (S)                  |
| 6       | Ia | B       | 2:1      | r.t.                | 5                  | 87        | 63 (S)                  |
| 7       | Ia | B       | 1:1      | r.t.                | 7                  | 91        | 62 (S)                  |
| 8       | Ia | B       | 1:2      | r.t.                | 17                 | 93        | 63 (S)                  |
| 9       | Ia | B       | 1:2      | r.t.                | 20                 | 93        | 59 (S)                  |
| 10      | Ia | B       | 1:1      | −20                 | 48                 | 37        | 65 (S)                  |
| 11      | Ib | B       | 1:1      | r.t.                | 0.5                | 98        | 46 (R)                  |
| 12      | Ib | B       | 1:1      | r.t.                | 1.5                | 99        | 66 (S)                  |
| 13      | Id | B       | 1:1      | 0                   | 7                  | 99        | 74 (S)                  |
| 14      | Id | B       | 1:1      | −20                 | 20                 | 98        | 80 (S)                  |
| 15      | Ie | B       | 1:1      | r.t.                | 5                  | 97        | 45 (S)                  |

While the invention has been described in detail and with reference to specific examples thereof, it will be apparent to one skilled in the art that various changes and modifications can be made therein without departing from the spirit and scope thereof.

What is claimed is:

1. A 1-substituted-2-diphenylphosphinonaphthalene represented by formula (I):

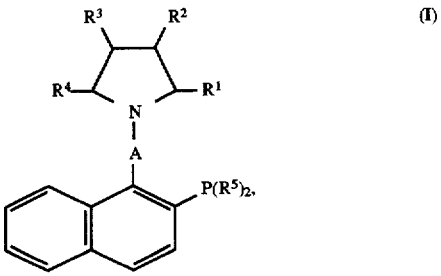

wherein at least one of $R^1$, $R^2$, $R^3$, and $R^4$, which may be the same or different, represents a lower alkyl group having 1 to 4 carbon atoms which may be substituted with an alkoxy group, a phenyl group or —$OR^6$ (wherein $R^6$ represents a hydrogen atom, a lower alkyl group having 1 to 4 carbon atoms or an alcohol-protective group), and the rest of them represent a hydrogen atom; A represents a single bond or a methylene group; and $R^5$ represents a substituted or unsubstituted phenyl group.

2. A transition metal complex of a transition metal of Groups 8–10 of the Periodic Table using the IUPAC new notation comprising, as a ligand, a 1-substituted-2-diphenylphosphinonaphthalene represented by formula (I):

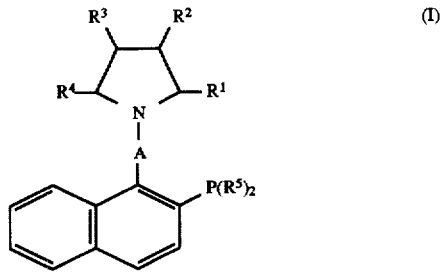

wherein at least one of $R^1$, $R^2$, $R^3$ and $R^4$, which may be the same or different, represents a lower alkyl group having 1 to 4 carbon atoms which may be substituted with an alkoxy group, a phenyl group or —$OR^6$, wherein $R^6$ represents a hydrogen atom, a lower alkyl group having 1 to 4 carbon atoms or an alcohol-protective group, and the rest of $R^1$, $R^2$, $R^3$ and $R^4$ represent a hydrogen atom; A represents a single bond or a methylene group; and $R^5$ represents a substituted or unsubstituted phenyl group.

3. The transition metal complex as claimed in claim 2, wherein said transition metal of Groups 8–10 of the Periodic Table using the IUPAC new notation is palladium, ruthenium or rhodium.

* * * * *